(12) United States Patent
Carr et al.

(10) Patent No.: US 8,865,015 B2
(45) Date of Patent: Oct. 21, 2014

(54) PRODUCTION OF POLYOL ESTER LUBRICANTS FOR REFRIGERATION SYSTEMS

(71) Applicant: Chemtura Corporation, Middlebury, CT (US)

(72) Inventors: Dale Carr, Morristown, NJ (US); Jeffrey Hutter, Edison, NJ (US); Richard Kelley, Princeton, NJ (US); Edward T. Hessell, Fairfield, CT (US); Roberto Urrego, Newington, CT (US)

(73) Assignee: Chemtura Corporation, Middlebury, CT (US)

(*) Notice: Subject to any disclaimer, the term of this patent is extended or adjusted under 35 U.S.C. 154(b) by 52 days.

(21) Appl. No.: 13/647,583

(22) Filed: Oct. 9, 2012

(65) Prior Publication Data
US 2014/0097379 A1    Apr. 10, 2014

Related U.S. Application Data (62) Division of application No. 12/691,300, filed on Jan. 21, 2010, now Pat. No. 8,318,647.

(51) Int. Cl.
*C09K 5/04*    (2006.01)

(52) U.S. Cl.
USPC .............................................. 252/68; 508/485

(58) Field of Classification Search
USPC .............................................. 252/68; 508/485
See application file for complete search history.

(56) References Cited

U.S. PATENT DOCUMENTS

| | | | | |
|---|---|---|---|---|
| 6,267,906 B1 * | 7/2001 | Schnur et al. | | 252/68 |
| 6,774,093 B2 * | 8/2004 | Carr et al. | | 508/485 |
| 7,387,746 B2 * | 6/2008 | Yamada et al. | | 252/68 |
| 2010/0190672 A1 * | 7/2010 | Carr et al. | | 508/485 |

* cited by examiner

*Primary Examiner* — John Hardee
(74) *Attorney, Agent, or Firm* — Joseph Suhadolnik; George Romanik; Chemtura Corporation

(57) ABSTRACT

A poly(neopentylpolyol) ester composition is produced by reacting a neopentylpolyol having the formula:

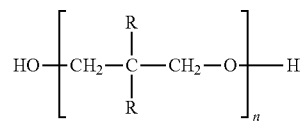

wherein each R is independently selected from the group consisting of $CH_3$, $C_2H_5$ and $CH_2OH$ and n is a number from 1 to 4, with at least one monocarboxylic acid having 2 to 15 carbon atoms in the presence of an acid catalyst and at an initial mole ratio of carboxyl groups to hydroxyl groups of greater than 0.5:1 to 0.95:1 to form a partially esterified poly(neopentylpolyol) composition. Then the partially esterified poly(neopentylpolyol) composition is reacted with additional monocarboxylic acid having 2 to 15 carbon atoms to form a final poly(neopentylpolyol) ester composition.

19 Claims, 4 Drawing Sheets

PRODUCTION OF POLYOL ESTER LUBRICANTS FOR REFRIGERATION SYSTEMS

CROSS REFERENCE TO RELATED APPLICATIONS

This patent application is a divisional of U.S. patent application Ser. No. 12/691,300, filed Jan. 21, 2010, now U.S. Pat No. 8,318,647, which claims the benefit of the filing dates of U.S. Prov. Application Nos. 61/147,182 filed Jan. 26, 2009 and 61/224,257 filed Jul. 9, 2009, the contents of which are incorporated herein by reference.

FIELD

This invention relates to the production of polyol ester lubricants and to the use of the resultant polyol esters in working fluids for refrigeration and air conditioning systems.

BACKGROUND

Polyol esters (POEs) are well known in the art as lubricants for displacement type refrigeration systems. Commonly used commercial POEs are derived from the reaction of a polyol (an alcohol containing 2 or more OH groups) with one or more monofunctional carboxylic acids. Such polyol esters are especially suited for use in systems utilizing hydrofluorocarbon refrigerants (HFCs), such as R-134a and related molecules, because their polar nature provides improved miscibility with the refrigerant in comparison to other lubricants such as mineral oils, poly-alpha-olefins, or alkylated aromatics. One example of such a polyol ester lubricant is disclosed in U.S. Pat. No. 6,221,272.

Dipentaerythritol (DiPE) is a key polyol ingredient in the manufacture of premium polyol esters for use as refrigeration lubricants. However, the supply of DiPE is highly dependent on the demand for monopentaerythritol (PE) since DiPE is a fractional by-product of PE manufacture. At certain times, the demand for PE drops and the supply of DiPE is very limited or non-existent. There is therefore a need to identify ways to reproduce the composition and performance of polyol esters derived from DiPE without having to use this expensive and possibly unavailable ingredient.

According to the present invention, a polyol ester composition has now been developed which is produced from PE as the polyol starting material but which has similar composition and properties as a polyol ester derived from DiPE. Moreover, by controlling the composition of the carboxylic acid mixture used to react with the PE, it is possible to produce ester compositions over a range of kinematic viscosity values but all having a high viscosity index.

U.S. Pat. No. 3,670,013 discloses a process for making a partially esterified poly(neopentylpolyol) product, which comprises introducing neopentyl polyol material, aliphatic monocarboxylic acid material and a catalytic quantity of acid catalyst material into a reaction zone, whereby a reaction mixture is formed, said neopentyl polyol material consisting essentially of at least one neopentyl polyol represented by the structural formula:

in which each R is independently selected from the group consisting of $CH_3$, $C_2H_5$ and $CH_2OH$, said aliphatic monocarboxylic acid material consisting essentially of at least one aliphatic hydrocarbon monocarboxylic acid, and said acid catalyst material consisting essentially of at least one acid esterification catalyst, wherein the initial concentration of said aliphatic monocarboxylic acid material in said reaction mixture is such as to provide an initial mole ratio of carboxyl groups to hydroxyl groups in the reaction mixture of from about 0.25:1 to about 0.5:1, and, while said reaction mixture is established and maintained at 170-200° C., aliphatic monocarboxylic acid vapor and water vapor are withdrawn from said reaction zone. The resultant partial esters are said to be useful as intermediates in the synthesis of the corresponding poly(neopentyl polyols), such as dipentaerythritol, and in the synthesis of the corresponding fully esterified poly(neopentyl polyols).

In addition, U.S. Pat. No. 5,895,778 discloses a synthetic coolant/lubricant composition comprising an ester mixture of: about 50 to 80 weight percent of polypentaerythritol ester formed by (i) reacting pentaerythritol with at least one linear monocarboxylic acid having from 7 to 12 carbon atoms in the presence of an excess of hydroxyl groups in a mole ratio of carboxyl groups to hydroxyl groups in the reaction mixture in a range from about 0.25:1 to about 0.50:1 and an acid catalyst to form partial polypentaerythritol esters and (ii) reacting the partial polypentaerythritol esters with an excess of at least one linear monocarboxylic acid having from 7 to 12 carbon atoms, and about 20 to 50 weight percent of a polyol ester formed by reacting a polyol having 5 to 8 carbon atoms and at least two hydroxyl groups with at least one linear monocarboxylic acid having from 7 to 12 carbon atoms, the linear acids including less than about five weight percent branched acids with the weight percents of the esters in the blend based on the total weight of the composition.

SUMMARY

In one aspect, the invention resides in a poly(neopentylpolyol) ester composition produced by:

(i) reacting a neopentylpolyol having the formula:

wherein each R is independently selected from the group consisting of $CH_3$, $C_2H_5$ and $CH_2OH$ and n is a number from 1 to 4, with at least one monocarboxylic acid having 2 to 15 carbon atoms in the presence of an acid catalyst and at an initial mole ratio of carboxyl groups to hydroxyl groups of greater than 0.5:1 to 0.95:1 to form a partially esterified poly(neopentylpolyol) composition; and (ii) reacting the partially esterified poly(neopentylpolyol) composition produced in (i) with additional monocarboxylic acid having 2 to 15 carbon atoms to form a final poly(neopentylpolyol)ester composition.

Conveniently, the initial mole ratio of carboxyl groups to hydroxyl groups of 0.7:1 to 0.85:1.

Conveniently, said neopentylpolyol has the formula:

wherein each of R is independently selected from the group consisting of $CH_3$, $C_2H_5$ and $CH_2OH$. In one embodiment, said neopentylpolyol comprises pentaerythritol.

Conveniently, said at least one monocarboxylic acid has 5 to 11 carbon atoms, such as 5 to 10 carbon atoms. Generally, said at least one monocarboxylic acid comprises one or more of n-pentanoic acid, iso-pentanoic acid, n-hexanoic acid, n-heptanoic acid, n-octanoic acid, n-nonanoic acid and iso-nonanoic acid (3,5,5-trimethylhexanoic acid). Preferably, said at least one monocarboxylic acid comprises a mixture of n-pentanoic acid and/or iso-pentanoic acid with iso-nonanoic acid, and optionally with n-heptanoic acid Conveniently, additional monocarboxylic acid employed in (ii) is the same as said at least one monocarboxylic acid employed in (i).

In one aspect, the invention resides in a poly(neopentylpolyol) ester composition produced by:

(i) reacting pentaerythritol with an acid mixture comprising a pentanoic acid, iso-nonanoic acid and optionally n-heptanoic acid in the presence of an acid catalyst and at an initial mole ratio of carboxyl groups to hydroxyl groups of greater than 0.5:1 to 0.95:1 to form a partially esterified poly(neopentylpolyol) composition; and (ii) reacting the partially esterified poly(neopentylpolyol) composition produced in (i) with additional amount of said acid mixture to form a final poly(neopentylpolyol) ester composition.

In a first embodiment, said acid mixture comprises a mixture of n-pentanoic acid, iso-nonanoic acid and optionally n-heptanoic acid comprising from about 2 to about 6 moles, preferably from about 2.5 to about 3.5 moles, of n-pentanoic acid and from about 0 to about 3.5 moles, preferably from about 2.5 to about 3.0 moles, of n-heptanoic acid per mole of iso-nonanoic acid (3,5,5-trimethylhexanoic acid) and said polyol ester composition has a kinematic viscosity at 40° C. of about 22 cSt to about 45 cSt, such as 28 cSt to about 36 cSt. Typically, said polyol ester composition has a viscosity index in excess of 130.

In a second embodiment, said acid mixture comprises a mixture of iso-pentanoic acid, n-heptanoic acid and iso-nonanoic acid comprising from about 1.75 to about 2.25 moles, preferably from about 1.9 to about 2.1 moles, of iso-pentanoic acid and 0.75 to about 1.25 moles, preferably from about 0.9 to about 1.1 moles, of n-heptanoic acid per mole of iso-nonanoic acid (3,5,5-trimethylhexanoic acid) and said polyol ester composition has a kinematic viscosity at 40° C. of about 46 cSt to about 68 cSt, such as 55 cSt to about 57 cSt. Typically, said polyol ester composition has a viscosity index in excess of 120.

In a third embodiment, said acid mixture comprises a mixture of iso-pentanoic acid, acid, iso-nonanoic acid and optionally n-heptanoic acid comprising from about 1 to about 10 moles, preferably from about 3 to about 4 moles, of iso-nonanoic acid and 0 to about 1 moles, preferably from about 0.01 to about 0.05 moles, of n-heptanoic acid per mole of iso-pentanoic acid (2-methylbutanoic acid) and said polyol ester composition has a kinematic viscosity at 40° C. of about 68 cSt to about 170 cSt, such as 90 cSt to about 110 cSt. Typically, said polyol ester composition has a viscosity index in excess of 95.

In yet a further aspect, the invention resides in a working fluid comprising (a) a refrigerant and (b) a poly(neopentylpolyol) ester composition produced by:

(i) reacting a neopentylpolyol having the formula:

wherein each R is independently selected from the group consisting of $CH_3$, $C_2H_5$ and $CH_2OH$ and n is a number from 1 to 4, with at least one monocarboxylic acid having 2 to 15 carbon atoms in the presence of an acid catalyst and at an initial mole ratio of carboxyl groups to hydroxyl groups of greater than 0.5:1 to 0.95:1 to form a partially esterified poly(neopentylpolyol) composition; and (ii) reacting the partially esterified poly(neopentylpolyol) composition produced in (i) with additional monocarboxylic acid having 2 to 15 carbon atoms to form a final poly(neopentylpolyol) ester composition.

Conveniently, the refrigerant is a hydrofluorocarbon, a fluorocarbon or a mixture thereof.

In yet a further aspect, the invention resides in a polyol ester composition comprising a mixture of esters of (a) monopentaerythritol, (b) dipentaerythritol and (c) tri- and higher pentaerythritols with at least one monocarboxylic acid having about 5 to about 10 carbon atoms, wherein the weight ratio of the esters is about 55 to about 65% of the monopentaerythritolesters, 15 to 25% of the dipentaerythritol esters and 15 to 25% of the tri- and higher pentaerythritol esters, such as about 60% of the monopentaerythritolesters, 20% of the dipentaerythritol esters and 20% of the tri- and higher pentaerythritol esters, and the polyol ester composition has a kinematic viscosity at 40° C. of about 46 cSt to about 68 cSt, such as 55 cSt to about 57 cSt. Typically, said polyol ester composition has a viscosity index in excess of 120. Conveniently, said at least one monocarboxylic acid having about 5 to about 10 carbon atoms comprises a mixture of iso-pentanoic acid, n-heptanoic acid and iso-nonanoic acid typically comprising from about 1.75 to about 2.25 moles, preferably from about 1.9 to about 2.1 moles, of iso-pentanoic acid and 0.75 to about 1.25 moles, preferably from about 0.9 to about 1.1 moles, of n-heptanoic acid per mole of iso-nonanoic acid (3,5,5-trimethylhexanoic acid). This polyol ester composition can be mixed with a refrigerant, such as a hydrofluorocarbon, a fluorocarbon or a mixture thereof, to form a working fluid for a refrigeration and/or an air conditioning system.

BRIEF DESCRIPTION OF THE DRAWINGS

FIGS. 3 (a), (b) and (c) are graphs of friction against slide roll ratio obtained when the ester composition of Example 3 and Emkarate RL 68H were subjected to a lubricity test using a Mini Traction Machine at a load of 30N, an average speed of 2 m/s and at temperatures of 40° C., 80° C. and 120° C. respectively.

DETAILED DESCRIPTION OF THE EMBODIMENTS

Described herein is a poly(neopentylpolyol) ester composition which is produced by a multi-stage process in which there is limited molar excess of hydroxyl groups in a first acid-catalyzed esterification and ether formation stage and additional monocarboxylic acid is added to a second stage to complete the esterification process. Using monopentaerythritol as the polyol starting material it is possible to produce a final poly(neopentylpolyol) ester composition which has similar composition and properties as a polyol ester derived by conventional means from a mixture of pentaerythritol and dipentaerythritol. The poly(neopentylpolyol) ester composition is therefore a desirable lubricant or lubricant basestock for a refrigeration working fluid.

Neopentylpolyol

The neopentylpolyol employed to produce the present polyol ester composition has the general formula:

wherein each of R is independently selected from the group consisting of $CH_3$, $C_2H_5$ and $CH_2OH$; and n is a number from 1 to 4. In one preferred embodiment, n is one and the neopentylpolyol has the formula:

wherein each of R is as defined above.

Non-limiting examples of suitable neopentylpolyols include monopentaerythritol, dipentaerythritol, tripentaerythritol, tetrapentaerythritol, trimethylolpropane, trimethylolethane, neopentyl glycol and the like. In some embodiments, a single neopentylpolyol, especially monopentaerythritol, is used to produce the ester lubricant, whereas in other embodiments two or more such neopentylpolyols are employed. For example, one commercially available grade of monopentaerythritol contains small amounts (up to 10 wt %) of dipentaerythritol, tripentaerythritol, and possibly tetrapentaerythritol.

Monocarboxylic Acid

The at least one monocarboxylic acid employed to produce the polyol ester composition has from about 2 to about 15 carbon atoms for example from about 5 to about 11 carbon atoms, such as from about 5 to about 10 carbon atoms. Typically the acid obeys the general formula:

$R^1C(O)OH$ wherein $R^1$ is a $C_1$ to $C_{14}$ alkyl, aryl, aralkyl or alkaryl group, such as a $C_4$ to $C_{10}$ alkyl group, for example $C_4$ to $C_9$ alkyl group. The alkyl chain $R^1$ may be branched or linear depending on the requirements for viscosity, viscosity index and degree of miscibility of the resulting lubricant with the refrigerant. In practice it is possible to use blends of different monobasic acids to achieve the optimum properties in the final lubricant.

Suitable monocarboxylic acids for use herein include acetic acid, propionic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, 3-methylbutanoic acid, 2-methylbutanoic acid, 2-ethylhexanoic acid, 2,4-dimethylpentanoic acid, 3,3,5-trimethylhexanoic acid and benzoic acid.

Generally, the at least one monocarboxylic acid comprises one or more of n-pentanoic acid, iso-pentanoic acid, n-hexanoic acid, n-heptanoic acid, n-octanoic acid, n-nonanoic acid and iso-nonanoic acid (3,5,5-trimethylhexanoic acid).

In a first embodiment, the at least one monocarboxylic acid comprises a mixture of n-pentanoic acid and iso-nonanoic acid, optionally with n-heptanoic acid, in which the mixture comprises from about 2 to about 6 moles, preferably from about 2.5 to about 3.5 moles, and most preferably 2.84 moles of n-pentanoic acid and from about 0 to about 3.5 moles, preferably from about 2.5 to about 3.0 moles, and most preferably 2.67 moles of n-heptanoic acid per mole of iso-nonanoic acid.

In a second embodiment, the at least one monocarboxylic acid comprises a mixture iso-pentanoic acid, n-heptanoic acid and iso-nonanoic acid, in which the mixture comprises from about 1.75 to about 2.25 moles, preferably from about 1.9 to about 2.1 moles, and most preferably about 2 moles, of iso-pentanoic acid and from about 0.75 to about 1.25 moles, preferably from about 0.9 to about 1.1 moles, and most preferably about 1 mole, of n-heptanoic acid per mole of iso-nonanoic acid (3,5,5-trimethylhexanoic acid).

In a third embodiment, the at least one monocarboxylic acid comprises a mixture of iso-pentanoic acid and iso-nonanoic acid, optionally with heptanoic acid, in which the mixture comprises from about 1 to about 10 moles, preferably from about 3 to about 4 moles, and most preferably 3.7 moles of iso-nonanoic acid and 0 to about 1 moles, preferably from about 0.01 to about 0.05 moles, and most preferably about 0.013 moles of n-heptanoic acid per mole of iso-pentanoic acid.

As used herein the term "iso-pentanoic acid" refers to the industrial chemical product which is available under that name and which is actually a mixture of about 34% 2-methylbutanoic acid and 66% n-pentanoic acid.

Production of the Poly(Neopentylpolyol) Ester Composition

The poly(neopentylpolyol) ester composition employed in the present working fluid is formed by a multi-step process.

In a first step, a neopentylpolyol, as defined above, and a $C_2$ to $C_{15}$ monocarboxylic acid or acid mixture are charged to a reaction vessel such that the mole ratio of carboxyl groups to hydroxyl groups is greater than 0.5:1 to 0.95:1, and typically is from 0.7:1 to 0.85:1. Also charged to the reaction vessel is at least one acid etherification catalyst, which typically is a strong acid catalyst, that is an acid having a pKa less than 1. Examples of suitable acid etherification catalysts include mineral acids, preferably, sulfuric acid, hydrochloric acid, and the like, acid salts such as, for example, sodium bisulfate, sodium bisulfite, and the like, sulfonic acids such as, for example, benzenesulfonic acid, toluenesulfonic acid, polystyrene sulfonic acid, methylsulfonic acid, ethylsulfonic acid, and the like.

The reaction mixture is then heated to a temperature of between about 150° C. and about 250° C., typically between about 170° C. and about 200° C., while acid vapor and water vapor are continuously removed from the reaction vessel, generally by the application of a vacuum source. The carboxylic acid, but not the water, removed during this step of the reaction is returned to the reactor and the reaction is continued until the desired quantity of water is removed from the reaction mixture. This can be determined by experimentation or may be estimated by calculating the expected amount of water of reaction. At this point when the starting neopentylpolyol is pentaerythritol, the mixture includes partial esters of pentaerythritol, dipentaerythritol, tripentaerythritol, tetrapentaerythritol and higher oligomeric/polymeric polyneopentylpolyols. Optionally, the acid catalyst may be neutralized with alkali at the end of the first reaction stage.

In order to complete the esterification of the partial esters, an excess of a $C_2$ to $C_{15}$ monocarboxylic acid or acid mixture acid or acid mixture and optionally an esterification catalyst is added to the reaction mixture. The additional acid can be the same or a different $C_2$ to $C_{15}$ monocarboxylic acid or acid mixture used in the initial step and is generally added in amount to provide a 10 to 25 percent excess of carboxyl groups, with respect to hydroxyl groups. The reaction mixture is then reheated to a temperature of between about 200° C. and about 260° C., typically between about 230° C. and about 245° C., with water of reaction being removed from the reaction vessel and acid being returned to the reactor. The use of vacuum will facilitate the reaction. When the hydroxyl value is reduced to a sufficiently low level, typically less than 1.0 mg KOH/g, the bulk of the excess acid is removed by vacuum distillation. Any residual acidity is neutralized with an alkali and the resulting poly(neopentylpolyol) ester is recovered and dried.

The resultant ester may be used without further purification or may be purified using conventional techniques such as distillation, treatment with acid scavengers to remove trace acidity, treatment with moisture scavengers to remove moisture and/or filtration to improve clarity.

Composition and Properties of the Poly(Neopentylpolyol) Ester Composition

The composition of the poly(neopentylpolyol) ester will depend on the particular neopentylpolyol and monocarboxylic acid employed to produce the ester. However, where the neopentylpolyol is pentaerythritol, the ester will typically have the composition and properties of an equivalent ester produced from mixtures of monopentaerythritol and dipentaerythritol by a conventional process.

Thus, where the neopentylpolyol is pentaerythritol and the carboxylic acid is a mixture of n-pentanoic acid, iso-nonanoic acid and optionally n-heptanoic acid according to said first embodiment described above, it is possible to produce a polyol ester with a kinematic viscosity at 40° C. of about 22 cSt to about 45 cSt, such as about 28 cSt to about 36 cSt, and a viscosity index in excess of 130.

Alternatively, where the neopentylpolyol is pentaerythritol and the carboxylic acid is a mixture of iso-pentanoic acid, n-heptanoic acid and iso-nonanoic acid according to said second embodiment described above, it is possible to produce a polyol ester with a kinematic viscosity at 40° C. of about 46 cSt to about 68 cSt, such as 50 cSt to about 60 cSt, and a viscosity index in excess of 120. The poly(neopentylpolyol) ester of this embodiment is also believed to have a novel composition in that the composition, as determined by gel permeation chromatography, comprises a mixture of esters of (a) monopentaerythritol, (b) dipentaerythritol and (c) tri- and higher pentaerythritols, wherein the weight ratio of the esters is about 55 to about 65%, such as 60%, of the monopentaerythritolesters, 15 to 25%, such as 20%, of the dipentaerythritol esters and 15 to 25%, such as 20%, of the tri- and higher pentaerythritol esters In addition, where the neopentylpolyol is pentaerythritol and the carboxylic acid is a mixture of iso-pentanoic acid, iso-nonanoic acid and optionally n-heptanoic acid according to said third embodiment described above, it is possible to produce a polyol ester with a kinematic viscosity at 40° C. of about 68 cSt to about 170 cSt, such as 90 cSt to about 110 cSt, and a viscosity index in excess of 95.

Values for kinematic viscosity at 40° C. and 100° C. reported herein are determined by ASTM Method D 445 and values for viscosity index reported herein are determined according to ASTM Method D 2270.

Use of the Poly(Neopentylpolyol) Ester Composition

The present polyol esters are particularly intended for use as lubricants in working fluids for refrigeration and air conditioning systems, wherein the ester is combined with a heat transfer fluid, generally a fluoro-containing organic compound, such as a hydrofluorocarbon or fluorocarbon; a mixture of two or more hydrofluorocarbons or fluorocarbons; or any of the preceding in combination with a hydrocarbon. Non-limiting examples of suitable fluorocarbon and hydrofluorocarbon compounds include carbon tetrafluoride (R-14), difluoromethane (R-32), 1,1,1,2-tetrafluoroethane (R-134a), 1,1,2,2-tetrafluoroethane (R-134), pentafluoroethane (R-125), 1,1,1-trifluoroethane (R-143a) and tetrafluoropropene (R-1234yf). Non-limiting examples of mixtures of hydrofluorocarbons, fluorocarbons, and/or hydrocarbons include R-404A (a mixture of 1,1,1-trifluoroethane, 1,1,1,2-tetrafluoroethane and pentafluoroethane), R-410A (a mixture of 50 wt % difluoromethane and 50 wt % pentafluoroethane), R-410B (a mixture of 45 wt % difluoromethane and 55 wt % pentafluoroethane), R-417A (a mixture of 1,1,1,2-tetrafluoroethane, pentafluoroethane and n-butane), R-422D (a mixture of 1,1,1,2-tetrafluoroethane, pentafluoroethane and iso-butane), R-427A (a mixture of difluoromethane, pentafluoroethane, 1,1,1-trifluoroethane and 1,1,1,2-tetrafluoroethane) and R-507 (a mixture of pentafluoroethane and 1,1,1-trifluoroethane).

The present polyol esters can also be used with non-HFC refrigerants such as R-22 (chlorodifluoromethane), dimethylether, hydrocarbon refrigerants such as iso-butane, carbon dioxide and ammonia. A comprehensive list of other useful refrigerants can be found in European Published Patent Application EP 1985681 A, which is incorporated by reference in its entirety.

A working fluid containing the polyol ester described above as the base oil may further contain mineral oils and/or synthetic oils such as poly-α-olefins, alkylbenzenes, esters other than those described above, polyethers, polyvinyl ethers, perfluoropolyethers, phosphoric acid esters and/or mixtures thereof.

In addition, it is possible to add to the working fluid conventional lubricant additives, such as antioxidants, extreme-pressure additives, antiwear additives, friction reducing additives, defoaming agents, profoaming agents, metal deactivators, acid scavengers and the like.

Examples of the antioxidants that can be used include phenolic antioxidants such as 2,6-di-t-butyl-4-methylphenol and 4,4'-methylenebis(2,6-di-t-butylphenol); amine antioxidants such as p,p-dioctylphenylamine, monooctyldiphenylamine, phenothiazine, 3,7-dioctylphenothiazine, phenyl-1-naphthylamine, phenyl-2-naphthylamine, alkylphenyl-1-naphthylamine, and alkylphenyl-2-naphthylamine; sulfur-containing antioxidants such as alkyl disulfide, thiodipropionic acid esters and benzothiazole; and zinc dialkyl dithiophosphate and zinc diaryl dithiophosphate.

Examples of the extreme-pressure additives, antiwear additives, friction reducing additives that can be used include zinc compounds such as zinc dialkyl dithiophosphate and zinc diaryl dithiophosphate; sulfur compounds such as thiodipropinoic acid esters, dialkyl sulfide, dibenzyl sulfide, dialkyl polysulfide, alkylmercaptan, dibenzothiophene and 2,2'-dithiobis(benzothiazole); sulfur/nitrogen ashless antiwear additives such as dialkyldimercaptothiadiazoles and methylenebis(N,N-dialkyldithiocarbamates); phosphorus compounds such as triaryl phosphates such as tricresyl phosphate and trialkyl phosphates; dialkyl or diaryl phosphates; trialkyl or triaryl phosphites; amine salts of alkyl and dialkylphosphoric acid esters such as the dodecylamine salt of dimethylphosphoric acid ester; dialkyl or diaryl phosphites; monoalkyl or monoaryl phosphites; fluorine compounds such as perfluoroalkyl polyethers, trifluorochloroethylene polymers and graphite fluoride; silicon compounds such as a fatty acid-modified silicone; molybdenum disulfide, graphite, and the like. Examples of organic friction modifiers include long chain fatty amines and glycerol esters.

Examples of the defoaming and profoaming agents that can be used include silicone oils such as dimethylpolysiloxane and organosilicates such as diethyl silicate. Examples of the metal deactivators that can be used include benzotriazole, tolyltriazole, alizarin, quinizarin and mercaptobenzothiazole. Furthermore, epoxy compounds such as phenyl glycidyl ethers, alkyl glycidyl ethers, alkylglycidyl esters, epoxystearic acid esters and epoxidized vegetable oil, organotin compounds and boron compounds may be added as acid scavengers or stabilizers.

Examples of moisture scavengers include trialkylorthoformates such as trimethylorthoformate and triethylorthoformate, ketals such as 1,3-dioxacyclopentane, and amino ketals such as 2,2-dialkyloxazolidines.

The working fluids comprising the esters of the invention and a refrigerant can be used in a wide variety of refrigeration and heat energy transfer applications. Examples include all ranges of air conditioning from small window air conditioners, centralized home air conditioning units to light industrial air conditioners and large industrial units for factories, office buildings, apartment buildings and warehouses. Refrigeration applications include small home appliances such as home refrigerators, freezers, water coolers and icemakers to large scale refrigerated warehouses and ice skating rinks. Also included in industrial applications would be cascade grocery store refrigeration and freezer systems. Heat energy transfer applications include heat pumps for house hold heating and hot water heaters. Transportation related applications include automotive and truck air conditioning, refrigerated semi-trailers as well as refrigerated marine and rail shipping containers.

Types of compressors useful for the above applications can be classified into two broad categories; positive displacement and dynamic compressors. Positive displacement compressors increase refrigerant vapor pressure by reducing the volume of the compression chamber through work applied to the compressor's mechanism. Positive displacement compressors include many styles of compressors currently in use, such as reciprocating, rotary (rolling piston, rotary vane, single screw, twin screw), and orbital (scroll or trochoidal). Dynamic compressors increase refrigerant vapor pressure by continuous transfer of kinetic energy from the rotating member to the vapor, followed by conversion of this energy into a pressure rise. Centrifugal compressors function based on these principles. Details of the design and function of these compressors for refrigeration applications can be found in the 2008 ASHRAE Handbook, HVAC systems and Equipment, Chapter 37; the contents of which are included in its entirety by reference.

The invention will now be more particularly described with reference to the following Examples.

In the Examples, the term "acid value" of a polyol ester composition refers to the amount of unreacted acid in the composition and is reported as amount in mg of potassium hydroxide required to neutralize the unreacted acid in 1 gram of the composition. The value is measured by ASTM D 974.

In the Examples, pour point values were determined according to ASTM D 97 and flash point values were determined according to ASTM D 92.

EXAMPLE 1

A reactor was equipped with a mechanical stirrer, thermocouple, thermoregulator, Dean Stark trap, condenser, nitrogen sparger, and vacuum source. To the reactor was charged pentaerythritol and a mixture of n-pentanoic acid, n-heptanoic acid and 3,5,5-trimethylhexanoic acid in the molar ratio indicated in Table 1 and in an amount so as to provide an acid:hydroxyl molar ratio of about 0.70:1. To the initial charge was added a strong acid catalyst as described by Leibfried in U.S. Pat. No. 3,670,013.

The mixture was heated to a temperature of about 170° C. and water of reaction was removed and collected in the trap. Vacuum was applied at temperature to obtain a reflux thereby removing the water and returning the acid collected in the trap to the reactor. The temperature was maintained at 170° C. under vacuum the desired amount of water was collected. This amount of water collected included the theoretical amount of water due to esterification along with the water due to the condensation (ether formation) of partially esterified pentaerythritol. At this point the reaction mixture consisted mostly of partial esters of pentaerythritol and dipentaerythritol, with small amounts of tripentaerythritol, tetrapentaerythritol.

After cooling the partially esterified product to about 134° C., an amount of pentanoic acid, heptanoic acid and 3,5,5-trimethylhexanoic acid sufficient to react with any free hydroxyl groups was charged, along with an amount of alkali sufficient to neutralize the strong acid catalyst used in the first step. Heat was then applied to raise the temperature of the reaction mixture to 240° C., whereafter the mixture was maintained at this temperature for about 8 hours and the water of reaction was collected until the hydroxyl value was 6.4 mg KOH/g.

The reaction mixture was then held at 240° C. for about 3 additional hours, with vacuum being applied to remove excess acid overhead. When the acid value was less than 1.0 mg KOH/g, the mixture was cooled to 80° C. and residual acidity was neutralized with alkali. The viscosity of the polyester product at 40° C. was 30 cSt and at 100° C. was 5.7 cSt. Other physical properties of the product are provided in Table 1.

Comparative Example 1

A polyol ester was produced from the reaction of a combination of technical grade pentaerythritol (90 wt % pentaerythritol and 10 wt % dipentaerythritol) and dipentaerythritol with a mixture of n-pentanoic acid, n-heptanoic acid and 3,5,5-trimethylhexanoic acid using a conventional process. A reactor equipped with a mechanical stirrer, thermocouple, thermoregulator, Dean Stark trap, condenser, nitrogen sparger, and vacuum source was charged with the polyols and the acid mixture in the ratios shown in Table 1 such that there was an approximately 15 molar % excess of acid groups to hydroxyl groups. The reaction mixture was heated to 240° C. and held at that temperature while the water of reaction was removed via the Dean Stark trap and the acids were returned to the reaction. The heating at 240° C. was continued until the hydroxyl value dropped to below 2.5 mg KOH/gram. The reaction was then held at 240° C. for about 3 additional hours, with vacuum being applied to remove excess acid overhead. When the acid value was less than 1.0 mg KOH/g, the mixture was cooled to 80° C. and residual acidity was neutralized with alkali. The viscosity of the polyester product at 40° C. was 30.1 cSt and at 100° C. was 5.7 cSt. Other physical properties of the product are provided in Table 1.

The esters of Example 1 and Comparative Example 1 were compared in Pin-on-Vee Block Test (ASTM D 3233 Method B), as described below, and the results are also reported in Table 1.

This Pin-on-Vee Block Test measures the extreme pressure load carrying performance of a lubricant. A steel journal held in place by a brass shear pin is rotated against two stationary V-blocks to give a four-line contact. The test pieces and their supporting jaws are immersed in the oil sample cup for oil lubricants. The journal is driven at 250 rpm and load is applied to the V-blocks through a nutcracker action lever arm and spring gage. The load is actuated and ramped continuously during the test by means of a ratchet wheel mechanism. The load is ramped by the loading ratchet mechanism until the brass shear pin shears or the test pin breaks. The torque is reported in pounds from the gauge attached to a Falex lubricant tester.

TABLE 1

|  | Comparative Example 1 | Example 1 |
|---|---|---|
| Raw Material Composition |  |  |
| Polyols (mole equivalent OH) |  |  |
| mono-Pentaerythritol | 100 |  |
| Technical Pentaerythritol |  | 82.6 |
| Dipentaerythritol |  | 17.4 |
| Acids (mole equivalent H+) |  |  |
| n-pentanoic acid | 43.63 | 43.15 |
| n-heptanoic acid | 41.00 | 41.38 |
| iso-nonanoic acid | 15.37 | 15.47 |
| Key Physical Properties |  |  |
| kinematic viscosity at 40° C. | 30.4 | 30.1 |
| kinematic viscosity at 100° C. | 5.74 | 5.7 |
| Viscosity Index | 132 | 131 |
| Acid Value (mg KOH/gram) | 0.01 | 0.03 |
| Density (lbs/gallon) | 8.235 | 8.29 |
| Pour Point, ° C. | −55 | −51 |
| Flash Point, ° C. | 270 | 282 |
| Performance |  |  |
| Miscibility range in R-410A (° C.) |  |  |
| 5 volume % | −43 +54 | −40 +57 |
| 10 volume % | −29 +46 | −26 +48.5 |
| 30 volume % | −23 +48 | −22 +48 |
| 60 volume % | <−60 >+60 | <−40 >+70 |
| ASTM D 3233 Falex Pin and Vee Block (Method B) | 1000+ | 1000+ |

Comparative Examples 1A to 1C

The process of Comparative Example 1 was repeated but with the mixture of pentaerythritol and dipentaerythritol being replaced with mono-pentaerythritol alone in Comparative Example IA and with technical pentaerythritol alone (90 wt % PE and 10 wt % diPE) in Comparative Example 1B. In Comparative Example 1C, the process of Comparative Example 1 was repeated but with the mixture of pentaerythritol and dipentaerythritol being replaced with mono-pentaerythritol alone and with a mixture of n-pentanoic acid, n-heptanoic acid and 3,5,5-trimethylhexanoic acid containing about 35 wt % of 3,5,5-trimethylhexanoic acid instead of the about 15 wt % employed in Table 1. The results are summarized in Table 2.

TABLE 2

|  | Comparative Example 1A | Comparative Example 1B | Comparative Example 1C |
|---|---|---|---|
| Raw Material Composition |  |  |  |
| Polyols (mole equivalent OH) |  |  |  |
| mono-Pentaerythritol | 100 |  | 100 |
| Technical Pentaerythritol |  | 100 |  |
| Acids (mole equivalent H+) |  |  |  |
| n-pentanoic acid | 43.15 | 43.15 | 31.8 |
| n-heptanoic acid | 41.38 | 41.38 | 32.8 |
| iso-nonanoic acid | 15.47 | 15.47 | 35.4 |
| Key Physical Properties |  |  |  |
| kinematic viscosity at 40° C. | 22.6 | 24.8 | 32.2 |
| kinematic viscosity at 100° C. | 4.66 | 4.93 | 5.73 |
| Viscosity Index | 125 | 125 | 125 |

From Tables 1 and 2, it will be seen that, using the conventional process of Comparative Example 1, dipentaerythritol is required to produce a polyester having a kinematic viscosity at 40° C. of 32 cSt and a VI of >130. Also, although it is possible to make an ISO 32 polyester by reacting mono-PE with an n-C5, n-C7 and iso-C9 acid mixture and shifting the acid composition to more iso-C9 (Comparative Example 1C), it will be seen that the resultant product has a VI of only 125.

EXAMPLE 2

The process of Example 1 was repeated but with the acid mixture comprising iso-pentanoic acid (as defined above), n-heptanoic acid and 3,5,5-trimethylhexanoic acid in the molar ratio indicated in Table 3 again in an amount so as to provide an acid:hydroxyl molar ratio of about 0.70:1. The viscosity of the polyester product at 40° C. was 100.7 cSt and at 100° C. was 11.25 cSt. The physical properties of the product are provided in Table 3. Compositional analysis of the product by gel permeation chromatography showed a mixture of monopentaerythritol esters, dipentaerythritol esters and polypentaerythritol esters in a weight ratio of about 76:16:8.

Comparative Example 2

The process of Comparative Example 1 was repeated but with the acid mixture comprising iso-pentanoic acid (as defined in Table 3), n-heptanoic acid and 3,5,5-trimethylhexanoic acid in the molar ratio indicated in Table 3 again in an amount so as to provide an approximately 15 molar % excess of acid groups to hydroxyl groups. The viscosity of the final polyester product at 40° C. was 93.7 cSt and at 100° C. was 11.0 cSt. The physical properties of the product are provided in Table 3.

The esters of Example 2 and Comparative Example 2 were compared in Pin-on-Vee Block Test (ASTM D 3233 Method B), as described above, and the results are reported in Table 3.

The wear preventive properties under boundary lubrication conditions of the esters of Example 2 and Comparative Example 2 were compared using the ASTM D 4172 4-Ball Wear Test. The results are reported in Table 3.

The thermal stability of the esters of Example 2 and Comparative Example 2 were evaluated using the ASHRAE 97 sealed tube test. In this test, the lubricant and refrigerant (0.7 mL each) are placed in a thick walled glass tube along with steel, copper and aluminum coupons. The aluminum coupon is placed in between the steel and copper. The tube is sealed under vacuum (after the proper amount of refrigerant has been condensed into the tube at low temperature) and the tubes are heated at 175° C. for 14 days. At the end of the test the coupons are evaluated for any staining or corrosion and the lubricant is evaluated by gas chromatography for any decomposition of the ester to acids. The results are reported in Table 3.

The hydrolytic stability of the esters of Example 2 and Comparative Example 2 were evaluated by accelerated heat aging at 120° C. First, the moisture content of a 100 gram aliquot of the lubricant is adjusted to contain 800±20 ppm water and placed in a 4 oz. glass jar with metal screw cap. A 50 gram aliquot is then placed in a 2 oz. glass jar which is then covered with tin foil and tightly sealed with a metal screw cap. The remaining sample in the 4 oz. jar is retained for later analysis. The 2 oz. jar is then placed in an oven at 120° C. for 7 days. The sample is cooled to room temperature. The acid value of both the heat aged and room temperature sample are measured by titration with 0.1 N KOH in isopropanol to a phenolphthalein endpoint. The difference between the acid value of the heat aged and room temperature sample is taken as the reported acid value for hydrolytic stability.

EXAMPLE 3

The process of Example 1 was repeated but with the acid mixture comprising 50 mole % iso-pentanoic acid (as defined above), 25 mole % n-heptanoic acid and 25 mole % 3,5,5-trimethylhexanoic acid again in an amount so as to provide an acid:hydroxyl molar ratio of about 0.70:1. The viscosity of the polyester product at 40° C. was 55 cSt and at 100° C. was 8.36 cSt. Compositional analysis of the product by gel permeation chromatography showed a mixture of monopentaerythritol esters, dipentaerythritol esters and polypentaerythritol esters in a weight ratio of about 60:20:20.

Comparative Example 3

Comparative Example 3 is a traditional premium ISO 68 polyol ester refrigeration lubricant commercially available from CPI Engineering Services under the tradename Emkarate RL 68H. Emkarate RL68H is the reaction product of an approximately 1:1 molar ratio of monopentaerythritol and dipentaerythritol with valeric acid, n-heptanoic acid and 3,5,5-trimethylhexanoic acid.

Table 4 compares the physical properties of the product of Example 3 with those of Comparative Example 3.

TABLE 3

|  | Test Method | Example 2 | Comparative Example 2 |
|---|---|---|---|
| Raw Material Composition Polyols (mole % equivalent OH) |  |  |  |
| mono-Pentaerythritol |  | 100 |  |
| Technical Pentaerythritol |  |  | 90.2 |
| Dipentaerythritol |  |  | 9.8 |
| Acids (mole equivalent H+) |  |  |  |
| iso-pentanoic acid |  | 21.2 | 21.2 |
| n-heptanoic acid |  | 0.3 | 0.3 |
| iso-nonanoic acid |  | 78.5 | 78.5 |
| Key Physical Properties |  |  |  |
| kinematic viscosity (40° C.) | ASTM D445 | 100.7 | 93.7 |
| kinematic viscosity (100° C.) | ASTM D445 | 11.25 | 11.0 |
| Viscosity Index | ASTM D2270 | 98 | 98 |
| Flash Point, ° C. | ASTM D92 | 263 | 263 |
| Pour Point, ° C. | ASTM D97 (auto) | −39 | −33 |
| Acid Value (mg KOH/gram) | ASTM D974 (mod) | 0.01 | 0.03 |
| Water content (wt %) | ASTM D1533 | 0.0025 | 0.0026 |
| Density, 15.6° C. (lbs/gallon) | ASTM D4052 | 8.12 | 8.06 |
| Performance |  |  |  |
| Miscibility range in R-134A (° C.) |  |  |  |
| 5 volume % |  | −45 >+70 | −48 >+70 |
| 10 volume % |  | −35 >+70 | −35 >+70 |
| 30 volume % |  | −34 >+70 | 26 >+70 |
| 60 volume % |  | −36 >+70 | −46 >+70 |
| Falex Pin and Vee Block Load test (lbs direct load) | ASTM D 3233 (Method A) | 650 | 650 |
| Four Ball Wear Test (wear scar diameter, mm) | ASTM D4172 | 0.93 | 0.96 |
| Sealed tube thermal stability in R-134a | ASHRAE 97 | Coupons shiny, No change in acid value of lubricant | Coupons shiny, No change in acid value of lubricant |
| Hydrolytic Stability |  | <0.5 | <0.5 |

TABLE 4

| Property | Example 3 | Comp. Example 3 | Method |
| --- | --- | --- | --- |
| ISO Viscosity Grade | 55 | 68 | ASTM 2422-86 |
| Kinematic Viscosity @ 40° C. | 55 | 685 | ASTM D-445 |
| Kinematic Viscosity @ 100° C. | 8.36 | 9.8 | ASTM D-445 |
| Viscosity Index | 125 | 120 | ASTM D-2270 |
| Water Content, ppm | <50 | <50 | ASTM D-1533 |
| Specific gravity | 1.00 | 0.9847 | ASTM D-4052 |
| Density @ 15.6° C., lbs/gal | 8.332 | 8.205 | ASTM D-4052 |
| Pour Point, ° C. | −51 | −39 | ASTM D-97 |
| Flash Point, ° C. | 257 | 260 | ASTM D-92 |
| ASTM Color | <1.0 | <0.5 | ASTM D-1500 |
| Acid Number (mg KOH/g) | <0.05 | 0.02 | ASTM D974-75 |
| Miscibility with R-134a | | | |
| 5 volume % | −37 >+70 | −45 >+70 | |
| 10 volume % | −35 >+70 | −31 >+70 | |
| 30 volume % | −39 >+70 | −23 >+70 | |
| 60 volume % | −60 >+70 | −60 >+70 | |
| Miscibility with R-410A | | | |
| 5 volume % | −24 +43 | −30 +50 | |
| 10 volume % | −17 +36 | −12 +38 | |
| 30 volume % | −26 +44 | Not miscible | |
| 60 volume % | −60 >+70 | −44 >+70 | |

It will be seen from Table 4 that the product of Example 3 exhibits similar or improved miscibility with the refrigerant R-134a than the Comparative Example 3 material and in particular exhibits improved miscibility with the refrigerant R-410A at 30 volume % concentration.

The lubricity of the product of Example 3 was compared with that of Comparative Example 3 at temperatures of 40° C., 80° C. and 120° C. using a Mini Traction Machine supplied by PCS Instruments. This MTM test measures the lubricity/frictional properties of lubricants by two different techniques using a rotating ball-on-disk geometry.

In a first mode of operation, the lubricity of the lubricant is measured under full fluid film conditions (hydrodynamic lubrication). The speed of the ball and disk are ramped simultaneously at a slide-roll-ratio of 50% and the coefficient of friction is measured as a function of entrainment speed at constant load and temperature (Stribeck Curve). This means that the ball is always moving at 50% of the speed of the rotating disk as the speed of the disk is ramped. As the speed of the disk and ball are increased there is a pressure build up at the front of the rolling/sliding contact due to the movement of the lubricant to either side of the metal-metal contact. At some point the speed becomes fast enough and the pressure becomes sufficient to result in lubricant entrainment between the ball and the disk contact. At this point the system is under hydrodynamic lubrication; meaning that the lubrication is controlled by the integrity of the film between the ball and disk. A lower coefficient of friction at high entrainment speeds indicates a lubricant with better lubricity performance.

In a second mode of operation, the lubricity is measured over the total range of lubrication regimes (boundary, mixed film, elastohydrodynamic and hydrodynamic). In this test, the coefficient of friction is measured at constant load and temperature at various slide/roll ratios (i.e., the ball and disk are rotated at different speeds relative to one another) (Traction Curve).

For both modes of operation the test is typically conducted at several different fixed temperatures; in this case 40, 80 and 120° C. and a load of 30 N. Coefficient of friction is a direct measurement of the lubricity of the lubricant; the lower the coefficient of friction, the higher the lubricity of the lubricant. It is important to note that for this test it is only meaningful to compare lubricants of equivalent ISO viscosity grade.

Figure 1:
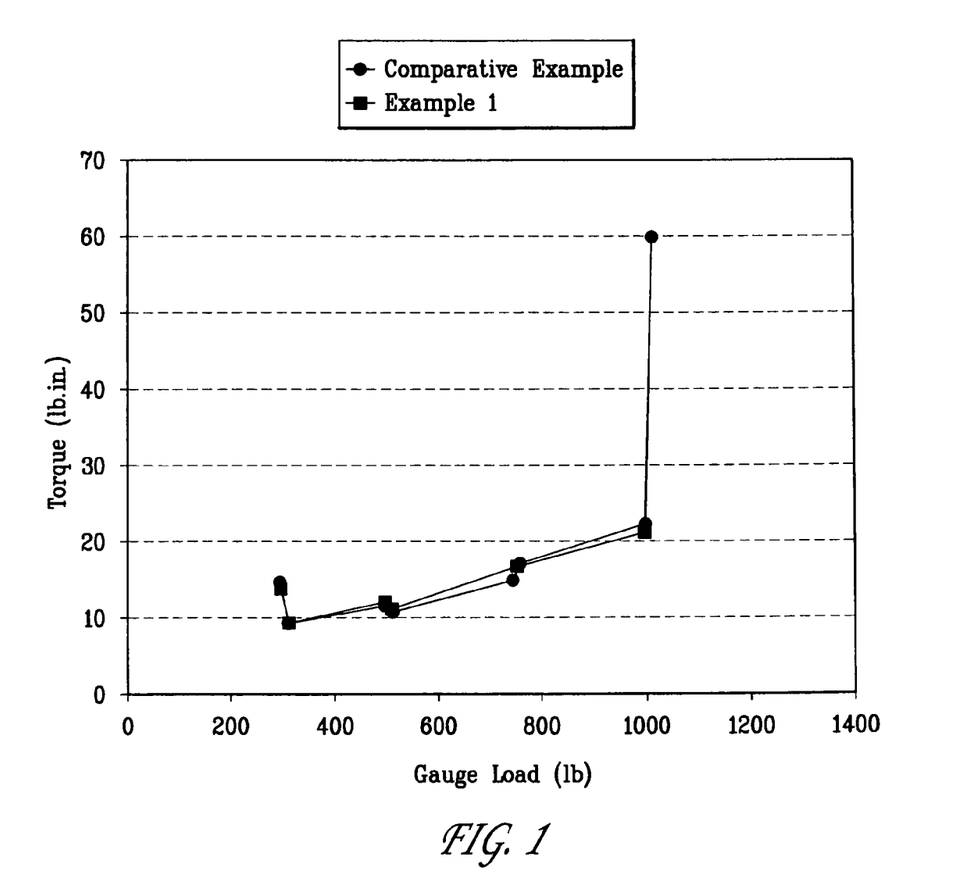
FIG. 1 is a graph of torque as a function of gauge load obtained when the lubricant of Example 1 and the lubricant of the Comparative Example were subjected to the Falex Pin and Vee block load carrying test.
Figure 2A:
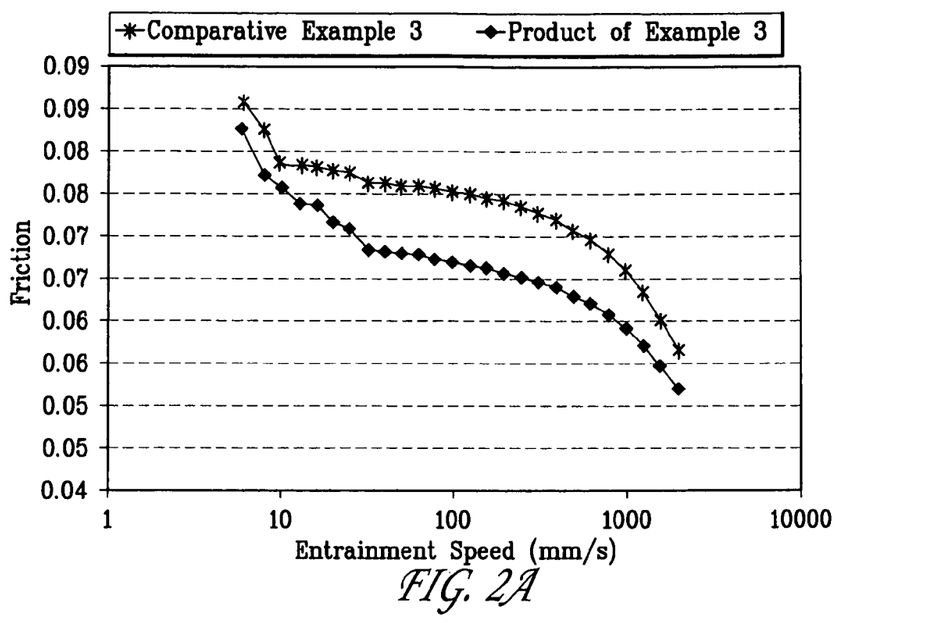
FIGS. 2(a), (b) and (c) are graphs of friction against entrainment speed obtained when the ester composition of Example 3 and a commercially available ISO 68 ester, Emkarate RL 68H, were subjected to a lubricity test using a Mini Traction Machine at a load of 30N and at temperatures of 40° C., 80° C. and 120° C. respectively.
Figure 2B:
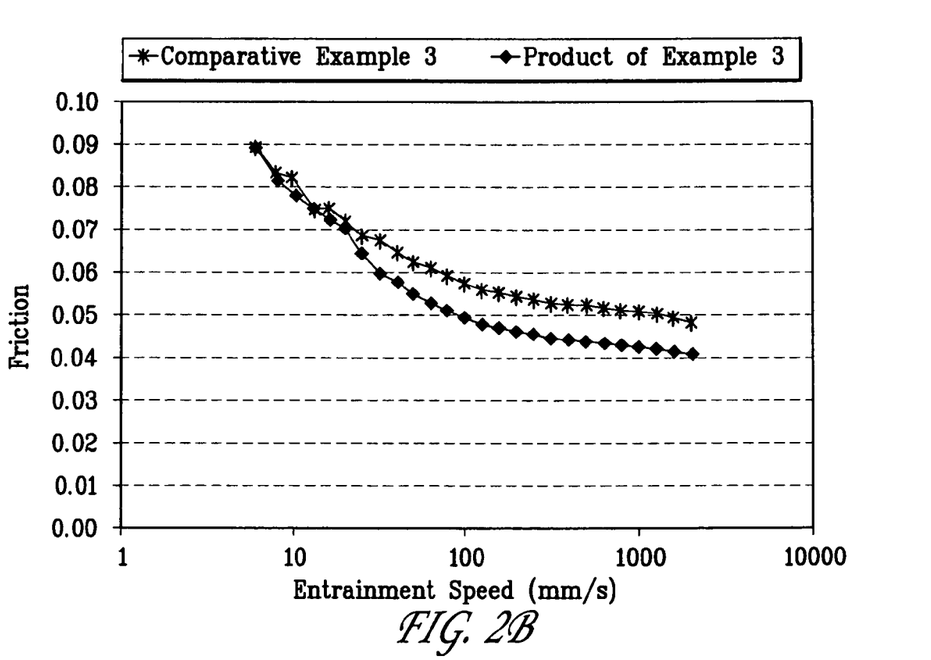
Figure 2C:
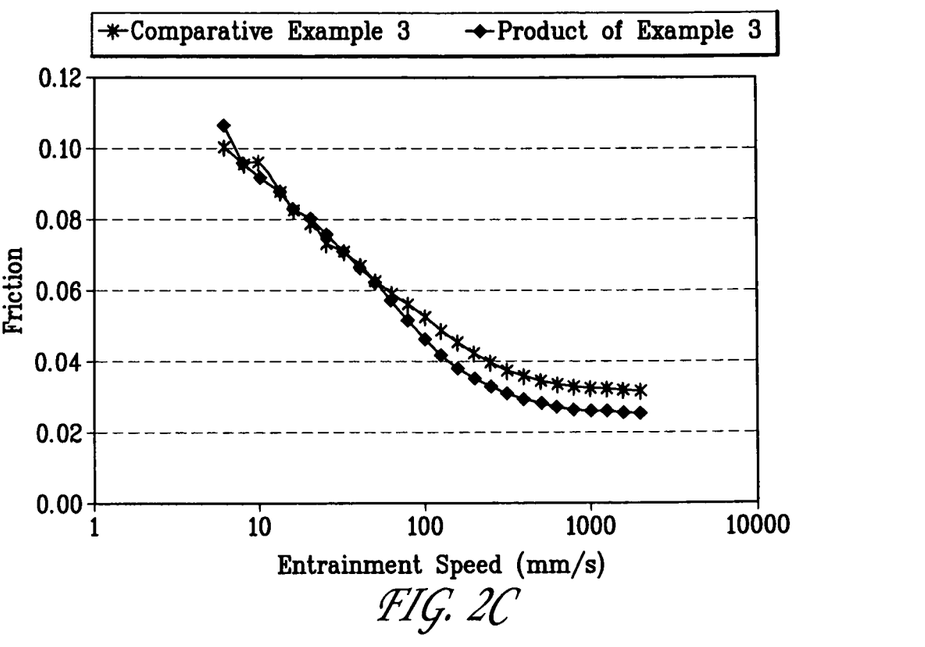
Figure 3A:
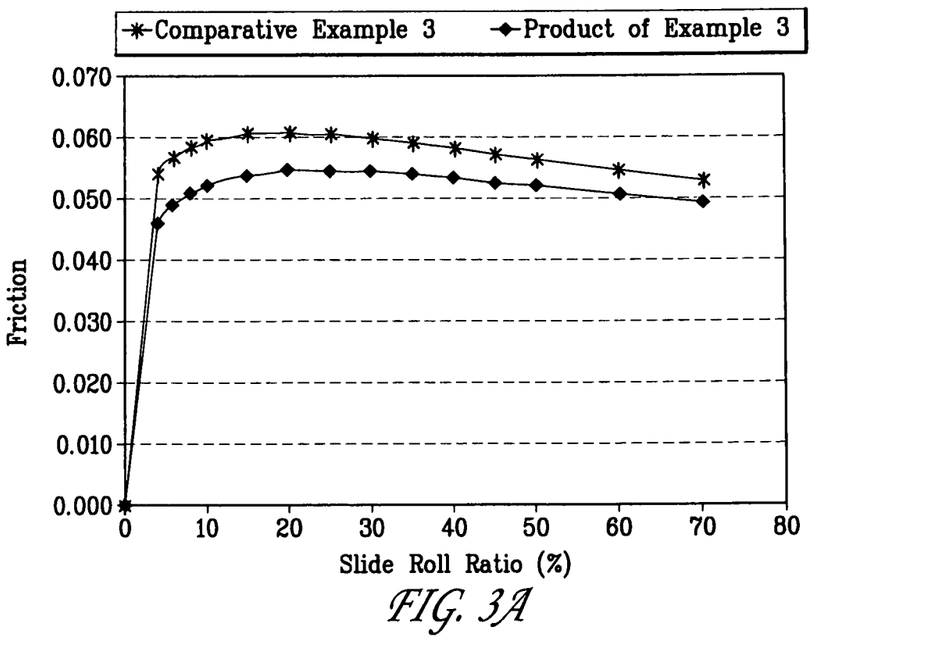
Figure 3B:
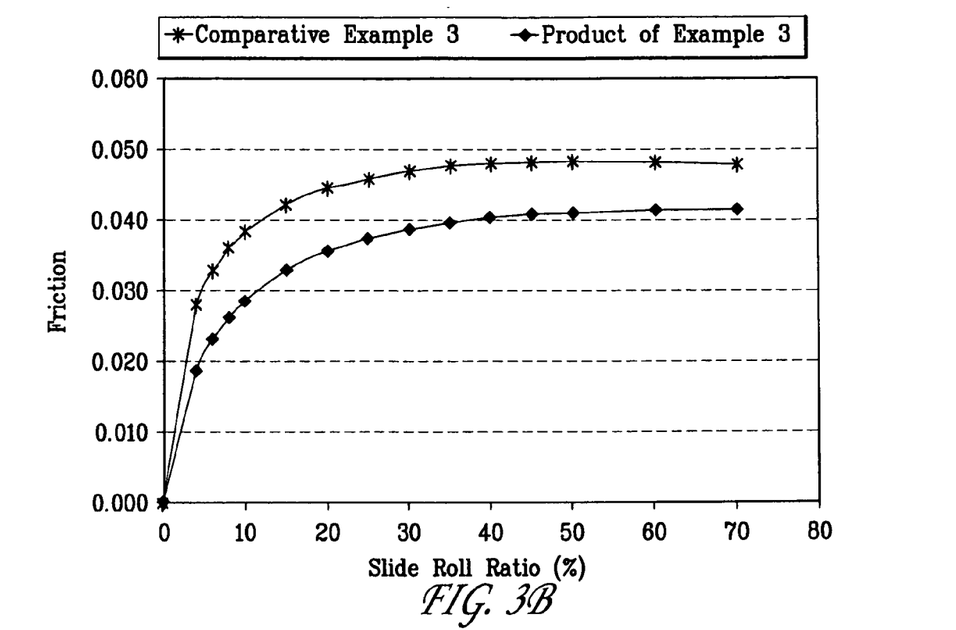
Figure 3C:
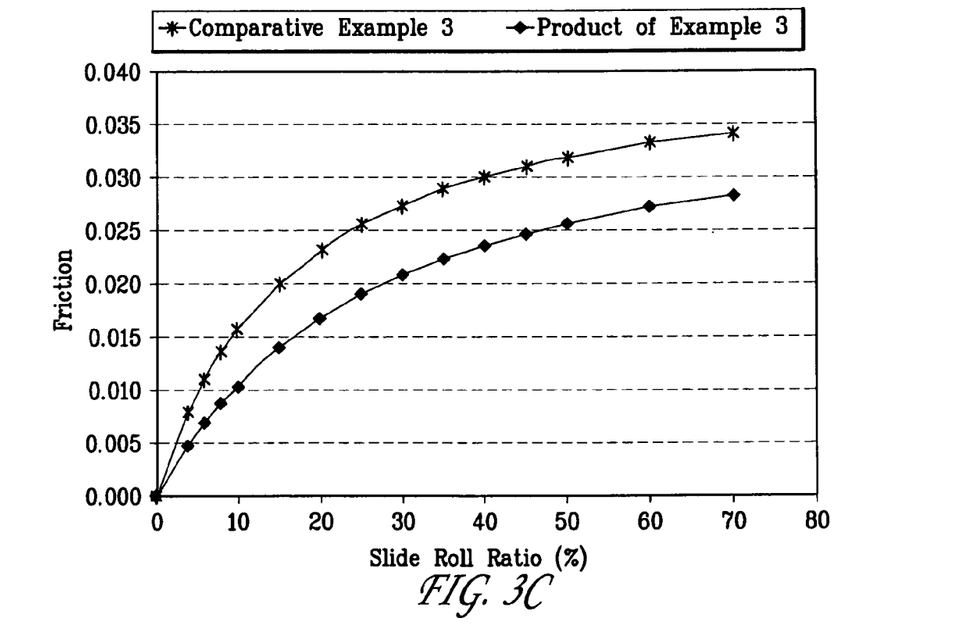

The results are shown in FIGS. 2(a) to (c) and FIGS. 3(a) to (c) and demonstrate that, despite its lower viscosity, the product of Example 3 exhibits lubricity and load carrying properties exceeding those of the Emkarate RL 68H material.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A poly(neopentylpolyol) ester composition produced by:
   (i) reacting a neopentyl polyol mixture comprising pentaerythritol and up to 10 wt% of dipentaerythritol, tripentaerythritol, and optionally tetrapentaerythritol, based on the combined weight of pentaerythritol, dipentaerythritol, tripentaerythritol and tetrapentaerythritol in the neopentyl polyol mixture, with one or more monocarboxylic acids having from 5 to 11 carbon atoms in the presence of an acid catalyst and at an initial mole ratio of carboxyl groups to hydroxyl groups of greater than 0.5:1 to 0.95:1 to form a partially esterified poly(neopentylpolyol) composition; and
   (ii) reacting the partially esterified poly(neopentylpolyol) composition produced in (i) with additional monocarboxylic acid, wherein the additional monocarboxylic acid employed comprises the same carboxylic acids employed in (i) and
   wherein the polyol ester composition comprises monopentaerythritol esters, dipentaerythritol esters and polypentaerythritol esters in a weight ratio of mono- to di- to polypentaerythritol esters of about 76:16:8 to about 60:20:20 and has a viscosity index in excess of 95.

2. The poly(neopentylpolyol) ester composition according to claim 1, wherein the initial mole ratio of carboxyl groups to hydroxyl groups is from 0.7:1 to 0.85:1.

3. The poly(neopentylpolyol) ester composition according to claim 1 wherein the one or more monocarboxylic acids comprises one or more monocarboxylic acids selected from n-pentanoic acid, iso-pentanoic acid, n-hexanoic acid, n-heptanoic acid, n-octanoic acid, n-nonanoic acid and iso-nonanoic acid.

4. The poly(neopentylpolyol) ester composition according to claim 3 wherein the one or more monocarboxylic acids comprises a mixture of monocarboxylic acids selected from n-pentanoic acid, iso-pentanoic acid, n-hexanoic acid, n-heptanoic acid, n-octanoic acid, n-nonanoic acid and iso-nonanoic acid, wherein said mixture of monocarboxylic acids comprises from about 2 to about 6 moles of n-pentanoic acid and from about 0 to about 3.5 moles of n-heptanoic acid per mole of iso-nonanoic acid.

5. A working fluid comprising (a) a refrigerant and (b) the poly(neopentylpolyol) ester composition according to claim 4.

6. The working fluid according to claim 5, wherein the refrigerant is a hydrofluorocarbon, a fluorocarbon or a mixture thereof.

7. The working fluid according to claim 6, wherein the refrigerant comprises a hydrofluorocarbon or fluorocarbon comound selected from difluoroethane (R-32) 1,1,1,2-tetrafluoroethane (R-134a), 1,1,2,2-tetrafluoroethane (R-134), pentafluoroethane (R-125) and tetrafluoropropene (R-1234yf).

8. The working fluid according to claim 6, wherein the refrigerant is selected from 1,1,1,2-tetrafluoroethane (R-134a), tetrafluoropropene (R-1234yf and a mixture of 50 wt% difluoromethane and 50 wt% pentafluoroethane (R-410A).

9. The poly(neopentylpolyol) ester composition according to claim 1 wherein said mixture of monocarboxylic acids comprises from about 1.75 to about 2.25 moles of n-pentanoic acid and 0.75 to about 1.25 moles of n-heptanoic acid per mole of iso-nonanoic acid.

10. The poly(neopentylpolyol) ester composition according to claim 1 produced by:
(i) reacting the neopentyl polyol mixture pentaerythritol with a mixture of monocarboxylic acids selected from n-pentanoic acid, iso-pentanoic acid, n-hexanoic acid, n-heptanoic acid, n-octanoic acid, n-nonanoic acid and iso-nonanoic acid, wherein said mixture comprises from about 1 to about 10 moles of iso-nonanoic acid and 0 to about 1 moles of n-heptanoic acid per mole of iso-pentanoic acid, in the presence of an acid catalyst and at an initial mole ratio of carboxyl groups to hydroxyl groups of greater than 0.5:1 to 0.95:1 to form a partially esterified poly(neopentylpolyol) composition; and
(ii) reacting the partially esterified poly(neopentylpolyol) composition produced in (i) with additional monocarboxylic acid, wherein the additional monocarboxylic acid employed comprises the same carboxylic acids employed in (i).

11. The poly(neopentylpolyol) ester composition according to claim 10 wherein the initial mole ratio of carboxyl groups to hydroxyl groups is from 0.7:1 to 0.85:1.

12. A working fluid comprising (a) a refrigerant and (b) the poly(neopentylpolyol) ester composition according to claim 10.

13. The working fluid according to claim 12, wherein the refrigerant is a hydrofluorocarbon, a fluorocarbon or a mixture thereof.

14. The working fluid according to claim 13, wherein the refrigerant comprises a hydrofluorocarbon or fluorocarbon comound selected from difluoroethane (R-32) 1,1,1,2-tetrafluoroethane (R-134a), 1,1,2,2-tetrafluoroethane (R-134), pentafluoroethane (R-125) and tetrafluoropropene (R-1234yf).

15. The working fluid according to claim 13, wherein the refrigerant is selected from 1,1,1,2-tetrafluoroethane (R-134a), tetrafluoropropene (R-1234yf and a mixture of 50 wt% difluoromethane and 50 wt% pentafluoroethane (R-410A).

16. A working fluid comprising (a) a refrigerant and (b) the poly(neopentylpolyol) ester composition according to claim 1.

17. The working fluid according to claim 16, wherein the refrigerant is a hydrofluorocarbon, a fluorocarbon or a mixture thereof.

18. The working fluid according to claim 17, wherein the refrigerant comprises a hydrofluorocarbon or fluorocarbon comound selected from difluoroethane (R-32) 1,1,1,2-tetrafluoroethane (R-134a), 1,1,2,2-tetrafluoroethane (R-134), pentafluoroethane (R-125) and tetrafluoropropene (R-1234yf).

19. The working fluid according to claim 17, wherein the refrigerant is selected from 1,1,1,2-tetrafluoroethane (R-134a), tetrafluoropropene (R-1234yf and a mixture of 50 wt% difluoromethane and 50 wt% pentafluoroethane (R-410A).

* * * * *